United States Patent [19]
Kline et al.

[11] Patent Number: 5,656,248
[45] Date of Patent: Aug. 12, 1997

[54] MULTI-STAGE INFECTIOUS WASTE TREATMENT SYSTEM

[75] Inventors: Daniel Kline, Carlsbad; Robert S. Meijer, San Diego, both of Calif.

[73] Assignee: Winfield Industries Inc., San Diego, Calif.

[21] Appl. No.: 492,296

[22] Filed: Jun. 19, 1995

Related U.S. Application Data

[63] Continuation-in-part of Ser. No. 214,597, Mar. 18, 1994, Pat. No. 5,425,925, which is a continuation-in-part of Ser. No. 690,116, Apr. 23, 1991, abandoned, which is a continuation-in-part of Ser. No. 511,275, Apr. 19, 1990, Pat. No. 5,089,228.

[51] Int. Cl.$^6$ ........................................ A61L 2/24
[52] U.S. Cl. ........................ 422/295; 422/105; 422/307; 422/309
[58] Field of Search .................... 422/105, 295, 422/26, 32, 307, 309; 241/17, 22

[56] References Cited

U.S. PATENT DOCUMENTS

| | | |
|---|---|---|
| 3,725,003 | 4/1973 | Moore et al. |
| 3,736,111 | 5/1973 | Gardner et al. |
| 4,265,636 | 5/1981 | Frankiewiez |
| 4,294,804 | 10/1981 | Baran |
| 4,576,792 | 3/1986 | Martensson |
| 4,578,185 | 3/1986 | Wilson et al. |
| 4,710,350 | 12/1987 | Petersen |
| 4,822,513 | 4/1989 | Corby |
| 4,884,756 | 12/1989 | Pearson |
| 4,908,188 | 3/1990 | Jefferis, III et al. |
| 4,923,677 | 5/1990 | Simon et al. |
| 4,966,755 | 10/1990 | Smith |
| 4,971,761 | 11/1990 | Johnson |
| 5,078,965 | 1/1992 | Pearson |
| 5,089,228 | 2/1992 | Meijer |
| 5,122,344 | 6/1992 | Schmoegner |

FOREIGN PATENT DOCUMENTS

| | | |
|---|---|---|
| 031516 | 5/1989 | European Pat. Off. |
| WO90/03949 | 4/1990 | European Pat. Off. |
| 0364367 | 4/1990 | European Pat. Off. |
| 0382018 | 8/1990 | European Pat. Off. |
| 0383553 | 8/1990 | European Pat. Off. |
| 0423817 | 4/1991 | European Pat. Off. |
| 2512024 | 12/1976 | Germany |
| 3317300 | 11/1984 | Germany |

OTHER PUBLICATIONS

Medical Safe TEC, Inc., Series Twelve Five, The Ultimate in Total Destruction and Decontamination of Infectious Waster, and Total Infectious Waste Disposal Specifications.
Bonnie Delaney, Smashing Success.

*Primary Examiner*—Timothy McMahon
*Attorney, Agent, or Firm*—Nydegger & Associates

[57] ABSTRACT

A multi-stage treatment system for infectious waste includes a shredding stage, a granulating stage, a wetting stage, a disinfecting stage, and a dewatering stage which define a continuous treatment flowpath for the infectious waste. A plurality of blades shred the waste in the shredding stage, then the waste is injected with volatile disinfectant chemicals which are mixed immediately before injection. A plurality of blades in a granulating stage then fragment the waste to a smaller particle size. The granulating stage insures that the waste is granulated to a sufficiently small size to facilitate the use of a relatively low concentration of a highly reactive disinfectant. Chemicals are mixed to form a volatile, highly reactive disinfectant which is then immediately injected into the waste downstream of the shredding stage. A plurality of jets wet the waste mixture in the wetting stage with the heated aqueous disinfectant. A flow restriction removes excess aqueous liquid from the disinfected waste in the dewatering stage and renders the product suitable for landfilling. A control system controls the temperature of the disinfectant to maintain an optimum temperature for a desired kill rate.

6 Claims, 7 Drawing Sheets

MULTI-STAGE INFECTIOUS WASTE TREATMENT SYSTEM

RELATED APPLICATIONS

This file is a continuation-in-part application of prior patent application for a "Multi-Stage Infectious Waste Treatment System", Ser. No. 214,597, filed Mar. 18, 1994 now U.S. Pat. No. 5,425,925, which is a continuation-in-part of an application for a "Method for Sterilizing and Disposing of Infectious Waste," Ser. No. 690,116, filed Apr. 23, 1991 now abandoned, which was a continuation-in-part of application Ser. No. 511,275, filed Apr. 19, 1990, now U.S. Pat. No. 5,089,228.

FIELD OF THE INVENTION

The present invention relates generally to treatment of infectious waste. More particularly, the present invention relates to a system which mechanically fragments and decontaminates infectious waste. The present invention is particularly, though not exclusively, useful for treating an infectious waste stream which includes a variety of types of waste.

BACKGROUND OF THE INVENTION

The disposal of infectious waste from hospitals and other medical establishments is a major problem. Indeed, the importance of proper and effective infectious waste disposal has become of greater concern in recent years, due to an increased awareness of health problems such as the AIDS epidemic. In part because of the AIDS epidemic, definitions of what constitutes "infectious waste" are being broadened. Consequently, the volume of infectious waste which must be disposed of is increasing. Accordingly, the need for a system or apparatus which will accomplish the safe, efficacious, and cost effective treatment of significant volumes of infectious waste for disposal is growing.

One method for decontaminating infectious waste involves incineration, wherein the waste is burned and the decontaminated ashes are properly disposed. An alternative treatment method is to disinfect the waste in a steam autoclave prior to waste disposal. While effective for their intended purposes, both incinerators and autoclaves present ancillary problems. Incinerators, for example, are difficult and costly to construct and are relatively expensive to maintain in an environmentally safe manner. Autoclaves too, present additional problems, such as odor, cost and operational complexity. Additionally, waste which has been disinfected by autoclaving typically requires further treatment procedures, such as incineration or shredding and granulation, prior to final disposition of the waste in such places as landfills.

With the above discussion in mind, alternative infectious waste treatment systems have been proposed to disinfect the waste in preparation for disposal. According to these proposals, a solid infectious waste is contacted with a disinfectant solution containing a chlorine compound to decontaminate the waste. The decontaminated waste may then be disposed in ordinary landfills.

Unfortunately, decontamination of waste using chlorine compounds presents certain technical complications. First, liquid disinfectant loses its disinfectant potency during prolonged storage. Thus, there is a need to use liquid disinfectant that is relatively "fresh" in order to achieve an acceptable degree of waste decontamination. Second, it is relatively difficult to ensure that an appropriate concentration of the disinfectant has contacted the waste during the treatment process. It is also important, however, to avoid applying too high a concentration of chlorine compound to the waste, in order to avoid undesirable results, such as corrosive effects and the release of toxic gases. Significant health risks are known to result from the discharge of chlorine to the environment.

The most commonly used disinfectant is sodium hypochlorite, typically as a one percent solution. The strength of the solution is dictated by the necessity of achieving a desired rate of bacteria kill in a given apparatus, resulting in a given rate of use of the disinfectant when operating at a given rate of throughput of waste. The use of a one percent solution results in the discharge of a significant amount of chlorine into the environment from the typical apparatus, either into the sewer or absorbed into the processed waste.

Because of its higher reactivity, chlorine dioxide is far more effective than sodium hypochlorite for the treatment of infectious waste. Chlorine dioxide also typically exists as a gas in solution, greatly enhancing the penetration of the disinfectant into the waste material. Chlorine dioxide can, if applied to properly granulated waste, achieve the necessary kill rate at a concentration of only about 50 ppm, or only about 0.005 percent, or 5 one-thousandths of the necessary concentration of sodium hypochlorite. Finally, the chlorine dioxide is far less environmentally persistent, rapidly disassociating into sodium chloride, water, and citric acid. When taking into account the rate of use of sodium hypochlorite in a typical process, and the required rate of use of properly applied chlorine dioxide to achieve the same kill rate, the sodium hypochlorite process results in the discharge to the environment of approximately ten thousand times as much of the treatment chemical. This means that the chlorine dioxide process results in the discharge to the environment of an amount of chlorine which is minuscule, compared to the amount of chlorine discharged by the sodium hypochlorite process.

Unfortunately, chlorine dioxide is very corrosive, highly unstable, and even explosive. It can not simply be substituted for sodium hypochlorite in a process. It must be used in an apparatus designed to properly generate and mix the chemical, and designed to properly granulate and handle the waste material to allow the use of a very low concentration of the chemical. Further, it is impractical to store chlorine dioxide, because it is an oxidizer and exposure to oxidizable impurities would consume a portion of the chlorine dioxide. Effective exclusion of oxidizable impurities from the storage tank would be difficult. Because of these difficulties, sodium hypochlorite is almost always used instead, even though it is less effective, and even though it results in increased chlorine contamination of the environment.

The present invention recognizes that liquid precursors of chlorine dioxide can be stored for relatively lengthy time periods without losing their potency. Further, these liquid precursors can be mixed to form chlorine dioxide immediately prior to injection into a waste stream, in a continuous process. Chlorine dioxide can be produced by the combination of sodium chlorite with a strong mineral acid, such as hydrochloric acid, or with a weak organic acid, such as citric acid. The use of a strong acid tends to produce high concentrations of chlorine dioxide more rapidly, and the process tends to be more difficult to control. Treatment of medical waste requires very low concentrations of chlorine dioxide produced in a slow and predictable manner. Therefore, the best choice for treatment of medical waste is the combination of sodium chlorite with a weak organic acid, such as citric acid. The resulting reaction is slow and predictable, and it is easily mediated by controlling the temperature of the solution.

The resulting solution can be used in a very low concentration to decontaminate infectious waste, if used in a system that mechanically reduces the particle size of the waste to the appropriate size. The present invention also recognizes the necessity for the correct interaction of certain critical structural features in the waste processing apparatus, to achieve the necessary intimate contact between the low concentration of chlorine dioxide and the waste material, and to properly handle the waste material to allow the conservative use of the chlorine dioxide.

Accordingly, it is an object of the present invention to provide a system for waste treatment in which chlorine dioxide precursors are appropriately mixed and then immediately blended with infectious waste to decontaminate the waste, while preventing excessive decomposition of the disinfectant, and while preventing any explosion hazard. Another object of the present invention is to provide a system for waste treatment which results in the reduction of waste particle size to an appropriate size to allow effective use of the disinfectant in a low concentration, while preventing clogging of the waste stream and while maximizing the recycling of the disinfectant. Finally, it is an object of the present invention to provide a system for waste treatment which is relatively easy and comparatively cost-effective to implement.

SUMMARY OF THE INVENTION

The present invention is a system for treating infectious waste comprising a series of continuous treatment stages. The multi-stage treatment system has an inlet stage at its front end which comprises an opening for receiving the infectious waste. The waste may be fed in any form through the opening, but in a preferred embodiment, the opening is sized to receive a sealed plastic bag in which the waste is packaged. The bags are fed through the opening into the system in their entirety. In this manner, waste handlers operating the present system need never come in direct contact with the infectious waste. The waste bag has a primary compartment containing the infectious waste, and it can have one or more secondary prefilled and sealed compartments containing other process additives in isolation from the waste, all of which are to be introduced into the system. As will be seen below, the entire contents of the bag are released from the bag and commingled during operation of the treatment system.

The inlet opening leads to a fragmenting chamber positioned therebelow, which encloses the shredding, wetting, and granulating stages of the system. The waste drops under the force of gravity from the inlet stage down into the shredding stage which comprises a plurality of opposingly rotating shredder blades. The shredding blades destroy the waste bag, spilling its contents into the fragmenting chamber. Any process additives contained in the bag become mixed with the waste in the shredding stage. The blades also function to break up any large frangible waste into small size particles.

The wetting stage is positioned immediately beneath the shredding stage to wet the small particle size shredded waste with the liquid chlorine dioxide treatment solution, as the waste falls through the shredding blades. The liquid disinfectant will more thoroughly mix with the waste material as the waste passes farther through the system. The wetting stage comprises a plurality of jets through which the liquid disinfectant is pumped, with the jets being positioned at the interior walls of the fragmenting chamber immediately beneath the shredding blades. The jets are directed radially into the chamber and are capable of producing a controlled spray of the liquid disinfectant into the waste mixture. The liquid disinfectant is preferably an aqueous chlorine dioxide solution containing some gaseous chlorine dioxide, which has been formed by the continuous mixing of liquid sodium chlorite and citric acid immediately prior to injection through the jets. The liquid disinfectant is also maintained at an elevated temperature immediately prior to injection. The temperature of the disinfectant is controlled according to the measured chlorine dioxide concentration in gas stripped from the solution. The heated liquid is then injected, to uniformly contact the falling waste mixture to form a hot mash. While the present invention in its preferred embodiment makes possible the use of chlorine dioxide as the disinfectant, the apparatus can be used with other disinfectants without departing from the spirit of the invention.

The granulating stage is provided beneath the wetting stage and comprises a plurality of specially designed blades mounted on a shaft so as to be rotatable against a plurality of stationary blades mounted on the walls of the fragmenting chamber to form cutting surfaces. The granulating blades rotate in a radial plane which is substantially parallel to the flow of the mash. At the cutting surfaces, the granulating blades break up the already small particle size waste into yet smaller particle sizes, to insure intimate contact between the treatment chemical and the waste material, and to cut any fibrous material which has not been previously fragmented by the shredding blades. The granulator blades are designed to allow the use of a plurality of cutting edges as the edges wear as a result of contact with hard materials. The blades also fully mix the components of the waste mash, thereby ensuring that the disinfectant chemicals in the liquid medium adequately contact the waste material to achieve the necessary kill rate with a relatively low concentration of the chemical.

A granulator is used instead of a hammer mill, because a hammer mill will not consistently and efficiently reduce the particle size of non-brittle materials, which constitute the majority of the medical waste stream. When such soft materials are passed through a hammer mill, the materials tend to pass through in crumpled form, rather than having a reduced particle size. This results in reduced contact between the disinfectant and the waste material.

A granulator is used at this stage instead of a shredder, because a shredder produces long strips of material. The strips tend to clog the shredder if used with a sizing screen, and they tend to become folded in accordion folds, thereby reducing contact between the disinfectant and the waste material. A shredder can also pass relatively large items unscathed. If a sizing screen were used downstream of a shredder at this point, it would quickly clog.

The output of the granulating stage is preferably fully wetted by the disinfectant solution, and it has a smaller granular particle size than the output of the shredding stage. The granulating stage is also designed with a sizing screen interacting with the specially designed blades to insure that the waste material is repeatedly cut and separated. The blades tend to press outwardly on the waste material in addition to cutting it, partially forcing the waste material through the screen. The blades also drag waste material cross the surface of the screen, thereby dispersing any tightly packed clumps of the material. This insures that the waste material does not clog the screen, and that it is reduced to the appropriate size to achieve thorough contact with the disinfectant, thereby allowing use of the desired low concentration of chemical.

The outlet from the fragmenting chamber incorporates the aforementioned screen functioning in cooperation with the granulating blades. The screen is sized to allow a selected smaller granular particle size waste to fall through the screen into a disinfectant reactor chamber below, while retaining any waste which has not been sufficiently granulated in the granulating stage. Waste which is retained by the screen is scooped up by the granulating blades rotating against the screen and returned to the associated cutting surfaces for additional particle size reduction until the waste is sufficiently small to pass through the screen. Up to this point substantially all of the work to convey the waste through the above-recited stages is performed by gravity.

The granulating stage is followed by the disinfecting stage. The disinfecting stage comprises a disinfectant reaction chamber preferably integral with an auger. The auger has two ends; a liquid medium collection tank and inlet port are at one end of the auger and a disinfected solid waste discharge port is at the other end. The auger is inclined upwardly to convey the waste from the inlet port to the disinfected solid waste discharge port. The length of the auger wherein the disinfection reaction occurs constitutes the disinfectant reaction chamber. The disinfection reaction is preferably completed by the time the waste reaches a point about two-thirds up the auger incline. The controlled rate at which the auger screw carries the waste up the incline to the discharge port enables a sufficient residence time for disinfection of the waste.

The disinfecting stage is combined with a dewatering stage. The dewatering stage comprises a conical flow restriction immediately prior to the discharge port. Although some of the liquid medium is removed from the waste by gravity at the lower end of the auger, the bulk of the liquid medium is removed from the waste by compressing the mash through the flow restriction. The final exit from the auger is positioned at or slightly beyond the point at which the conical flow restriction begins. The conical flow restriction is constructed with a critical restriction angle best suited to dewater the waste being treated. When these features are combined with the proper granulating of the waste, and when the waste is free of long strips, a high degree of dewatering will result without resulting in clogging of the discharge path. The auger is also sloped at a critical angle best suited to assist in dewatering while avoiding clogging. The combination of the pressure rise in the mash resulting from the conical restriction, and the pressure rise resulting from the angle of the auger, yield a compression of the waste material which achieves the maximum dewatering efficiency without resulting in clogging.

The liquid medium driven from the waste mash exits the auger through perforations or a screen in the housing surrounding the auger, and the liquid is collected and passed to the heated disinfectant mixing tank for recycling to the wetting stage. The screen in the auger housing is shaped to conform to the radial edges of the auger, so that as the auger turns it continually scrapes compacted waste material from the screen. This prevents clogging of the screen. The liquid to be recycled is passed through a cyclone separator designed to remove heavy fines or other material prior to return of the liquid to the jets. The heavy fines or other material can be periodically dumped from the cyclone separator onto the waste material in the auger.

In operation, process control for the present system is provided by regulating the disinfectant concentration in the system and the liquid medium temperature. Temperature is related to the rate of liquid medium flow, and heater and auger operating parameters. The above-described system satisfies the present objective of providing an infectious waste treatment apparatus which contacts an infectious waste with precise amounts of a disinfectant to disinfect the waste while simultaneously fragmenting the waste to reduce its bulk volume. The system also provides an infectious waste disposal apparatus which is relatively easy and comparatively cost-effective to implement and operate.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
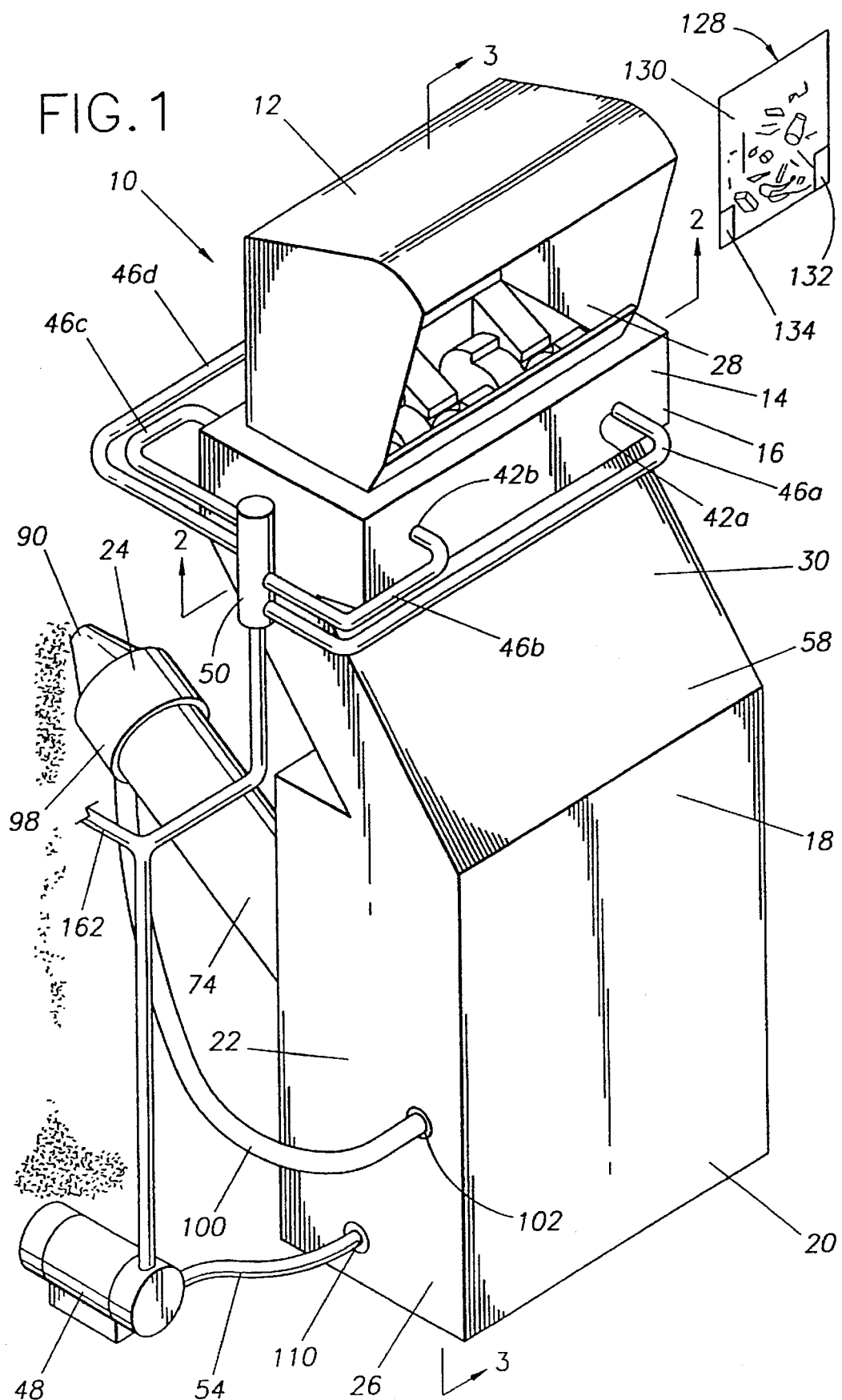
FIG. 1 is a perspective view of the multi-stage waste treatment apparatus of the present invention.
Figure 3:
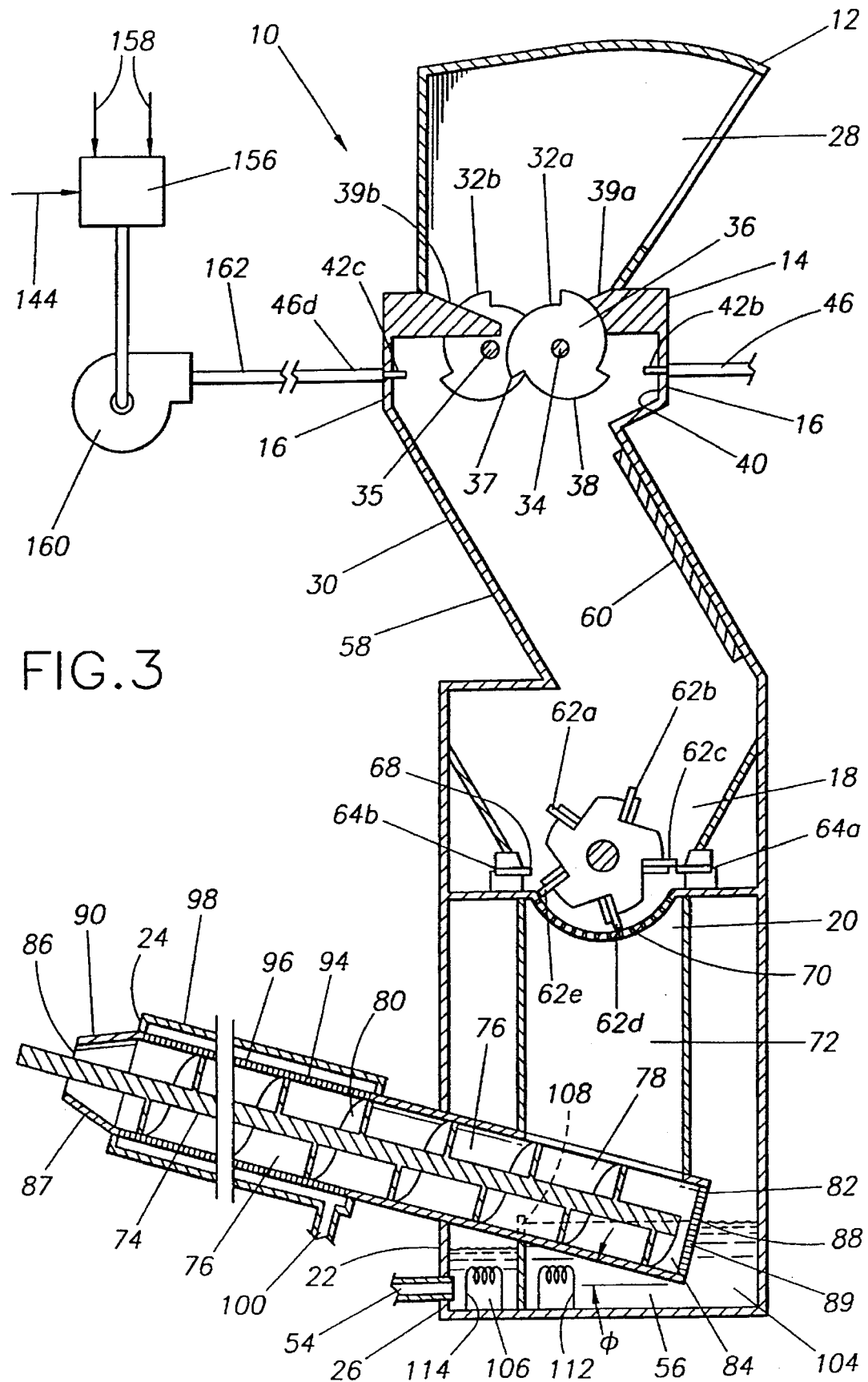
FIG. 3 is a schematic view of the apparatus of FIG. 1.

Referring initially to FIGS. 1 and 3, the infectious waste treatment system of the present invention is generally designated 10. System 10 comprises a plurality of treatment stages including an inlet stage 12, a shredding stage 14, a wetting stage 16, a granulating stage 18, a disinfecting stage 22, and a dewatering stage 24, which define a continuous flowpath for the waste. The terms "disinfect" and "decontaminate" are used synonymously herein and refer to the destruction of a substantial portion of infectious constituents within the infectious waste sufficient to render the waste substantially noninfectious.

Figure 2:
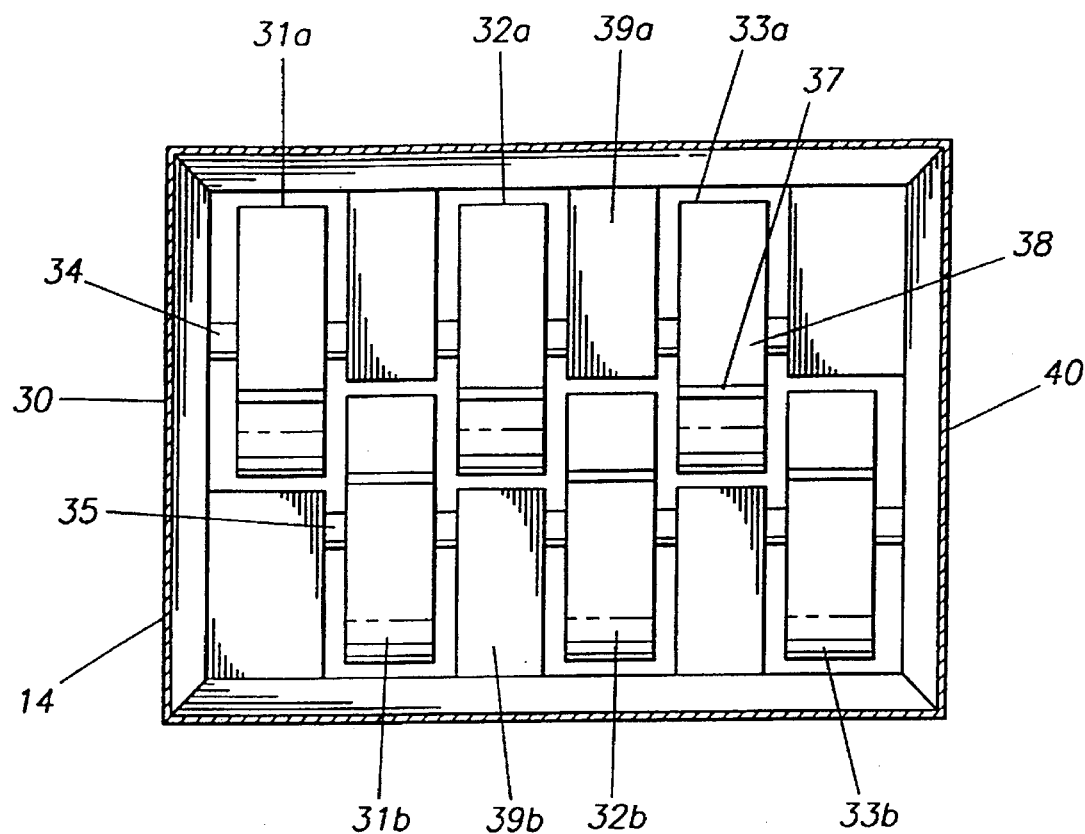
FIG. 2 is a view of the shredding stage of the apparatus of FIG. 1, along line 2—2.

Inlet stage 12 comprises an opening 28 at or near the top of a fragmenting chamber 30 which houses stages 14, 16, and 18. Inlet stage 12 opens down into shredding stage 14 at the upper level of fragmenting chamber 30. As shown in FIG. 2, shredding stage 14 comprises multiple pairs of rotatable shredding blades 31a,b, 32a,b, 33a,b. Blades 31a, 32a, 33a, are mounted on shaft 34 and blades 31b, 32b, 33b are mounted on shaft 35 such that blade 31b is rotatably fitted between blades 31a, 32a and so on for all the blades as shown. Each rotatable shredding blade is a disk 36 having a plurality of hook-shaped teeth 37 about the periphery 38 of disk 36. Stationary shredding blades such as 39a, 39b are fixed to chamber walls 40 spaced appropriately from rotatable blades 31a, 32a, 33a and 31b, 32b, 33b to channel waste into the rotatable blades, to reduce the waste particle size to a first selected particle size, and to prevent waste from accumulating in shredding stage 14. The output of waste material from the shredding stage 14 will include some long strips of relatively soft material. Shafts 34, 35 are positioned horizontally and parallel to one another, and the rotatable blades rotate in vertical planes which are substantially parallel to the vertical flowpath of the waste. Shredding action is provided by rotating shaft 34 in the opposite direction from shaft 35.

Referring to FIG. 3, a wetting stage 16 is provided immediately downstream from shredding stage 14. Wetting stage 16 comprises a plurality of liquid disinfectant jets 42a,b,c,d which are mounted in the wall 40 of chamber 30 around the periphery of the waste flowpath and adjacent the bottom side of the shredding blades. A liquid medium feed line is connected to each jet. Thus, as shown in FIG. 1, liquid medium feed lines 46a,b,c,d are connected to jets 42a,b,c,d respectively. Feed lines 46a,b,c, are also connected to a recycle pump 48 across a liquid distribution manifold 50. Pump 48 receives liquid medium from a recycle line 54 connected to a liquid medium collection tank 56 of a recycle stage 26. The manifold 50 is also fed by the output of a disinfectant mixing tank 156. Precursors, or constituents, of the desired disinfectant are fed into the mixing tank 156 through inlet lines 158. The disinfectant thus formulated is then immediately pumped from the mixing tank 156 into the manifold 50 by pump 160 and disinfectant line 162. This arrangement is particularly useful where the desired disinfectant is very volatile, such as chlorine dioxide. The liquid precursors can be sodium chlorite and citric acid. Recycled disinfectant can be fed back into the mixing tank through a recycle line 144. Recycle line 144 can be fed by a cyclone separator as will be discussed later. The mixing tank 156 can be maintained at a selected elevated temperature by heaters in the tank.

If it is desired to remove metals from the waste stream after shredding and wetting, a metal segregating stage 58 may be provided immediately after stages 14, 16. Metal segregating stage 58 comprises a magnet 60 which is mounted in the wall 40 of chamber 30. Magnet 60 contacts the waste as it falls toward granulating stage 18 to segregate the metals therefrom. Access is provided in wall 40 to enable periodic removal of metals from magnet 60.

Figure 7:
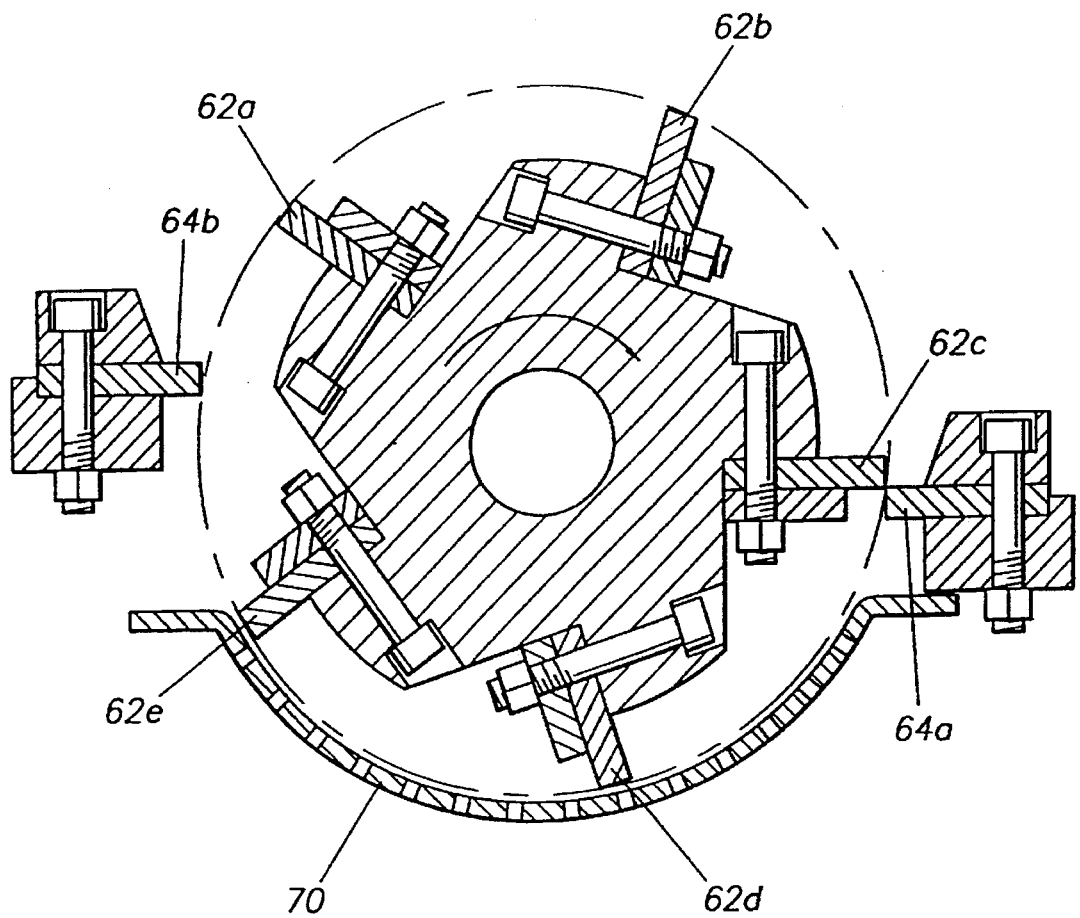
FIG. 7 is a schematic view of the granulating stage of the apparatus of FIG. 1.
Figure 8:
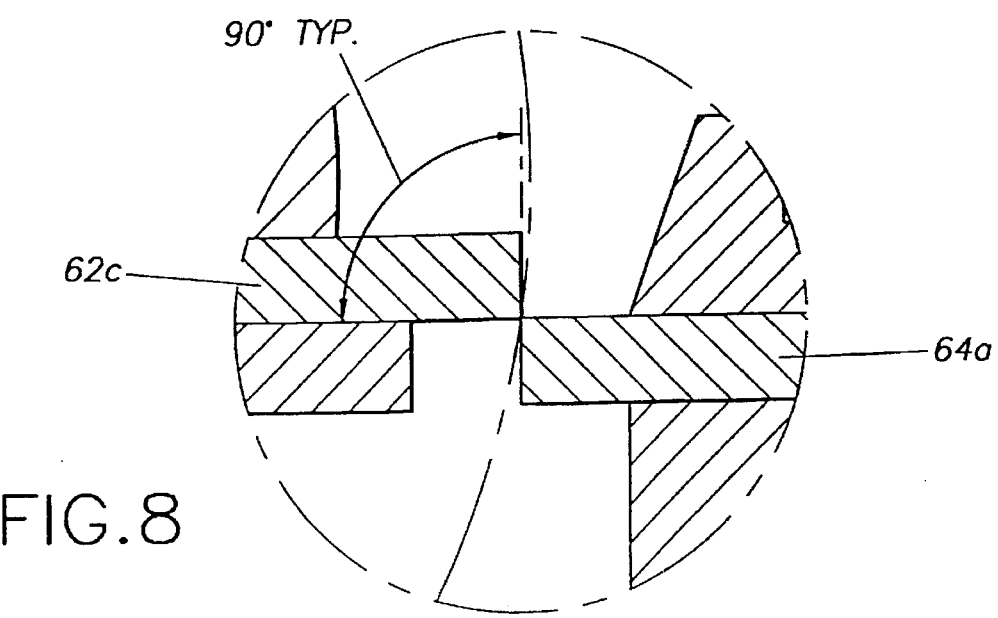
FIG. 8 is an enlarged view of a portion of FIG. 7, showing the relationship between the blades in the granulating stage.

Granulating stage 18 is positioned at the lower level of fragmenting chamber 30 and comprises a plurality of rotatable granulating blades 62a,b,c,d,e and stationary granulating blades 64a,b. Referring to FIGS. 3, 7, and 8, the rotatable blades 62a,b,c,d,e are mounted on a rotating shaft 66 which in turn is rotatably mounted on chamber wall 40. The rotatable blades have a vertical plane of rotation which is substantially parallel to the vertical flowpath of the waste. The rotatable blades 62a,b,c,d,e are rotatable past stationary granulating blades 64a, 64b, each of which is fixably mounted on opposite sides of chamber wall 40 adjacent rotatable blades 62a,b,c,d,e. As rotatable blades 62a,b,c,d,e rotate, they periodically pass stationary blades 64a,b to form transient cutting surfaces. FIG. 3 shows rotatable blade 62e meeting stationary blade 64b to form transient cutting surface 68. The rotatable and stationary granulating blades are all preferably formed with rectangular cross-sections as shown, so that each blade has four potential cutting edges. FIG. 8 shows the relationship between the cutting edges in more detail. Each blade can be removed and rotated to expose a new cutting edge, until all four edges on each blade have been dulled. As each rotatable blade passes each stationary blade, the clearance between the cutting edges is sufficiently small to granulate the material by a cutting action. The material is then continually passed through the blades until sufficient cuts have been made to reduce the waste material to a selected second, smaller particle size. In addition, all strips of waste material are granulated by this cutting action.

A screening action is accomplished immediately beneath the granulating blades in granulating stage 18. This comprises a screen 70 stretched cross-sectionally across conduit 72 which connects fragmenting chamber 30 and auger 74. Screen 70 has a mesh size which allows particles at or below a given particle size to pass through while preventing particles having a larger particle size than the given particle size from passing through. The movement of the rotatable blades imparts an outward radial motion to the waste material which partially imbeds the waste material in the screen 70. Screen 70 preferably has a ½ inch mesh size although other mesh sizes are within the purview of the skilled artisan. Screen 70 is positioned to cooperate with the rotatable granulating blades 62a,b,c,d,e of granulating stage 18. As the rotatable blades rotate, they periodically pass screen 70 to scoop waste retained on screen 70. FIG. 7 shows rotatable blade 62d meeting screen 70 to return waste retained by screen 70 to cutting surface 68.

Disinfecting stage 22 comprises a disinfectant reaction chamber 76 which is integral with auger 74. Auger 74 is inclined upward away from auger inlet 78 to enable precise control of the waste residence time in reaction chamber 76 and to facilitate dewatering as described hereafter. The inclination angle of auger 74 is defined as $\phi$. For a waste stream composed mostly of soft material, such as medical waste, $\phi$ is selected between about 10° and 20° and preferably about 15°. This aids in dewatering, without promoting clogging. A lesser angle results in less dewatering capability, while a greater angle appreciably increases the tendency to clog. Reaction chamber 76 is sufficiently sized to hold the throughput of system 10 for a residence time which enables disinfection of the waste before discharge from system 10. Auger 74 has a screw 80 extending axially the entire length of auger 74 which is rotatably mounted therein to carry waste from auger inlet 78 to a waste solid discharge port 86 at the upper end of auger 74.

Dewatering stage 24 is likewise integral with auger 74 and comprises a conical flow restriction 90 at solid disinfected waste discharge port 86. A portion of liquid medium exits auger 74 under gravity through port 82 to collection tank 56 in fluid communication with port 82. A perforated plate 88 is provided at port 82 having a plurality of perforations 89, each significantly smaller than the mesh size of screen 70, and preferably about ⅛ inch, to prevent substantial quantities of waste from exiting auger 74 thereat. However, the primary function of port 82 is to enable fluid intrusion into auger 74 as will be shown.

Figure 4:
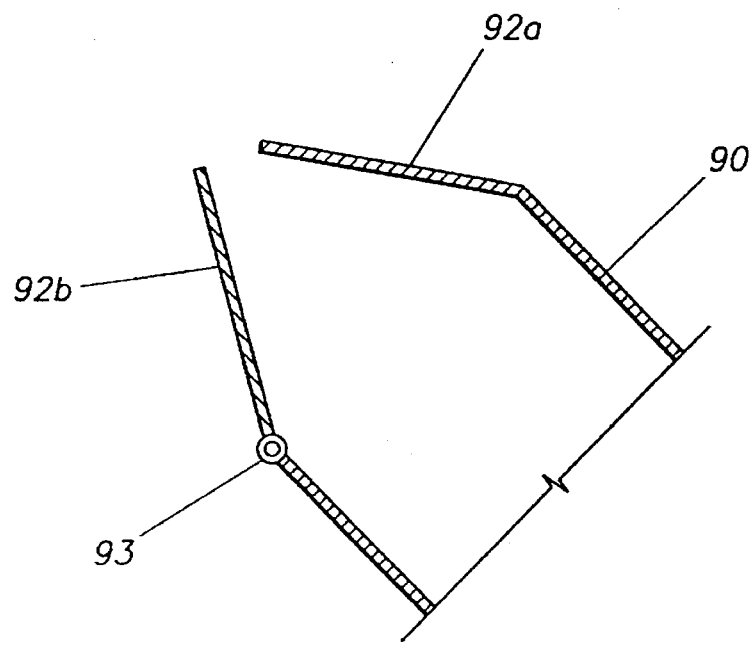
FIG. 4 is a section view of an alternate embodiment of the waste outlet flow restriction.

The conical flow restriction 90 imposes a pressure on the waste material which compacts the material and removes the bulk of liquid medium from the waste before it exits system 10. The auger screw 80 terminates slightly beyond the entrance to the conical restriction 90. In one embodiment the constriction is a conical nozzle 90 having a fixed opening at the end of waste discharge port 86. The angle of the conical restriction 90 is selected according to the content of the waste stream. For a waste stream composed mostly of soft material, such as medical waste, the angle is between 15 and 20 degrees, and preferably about 18 degrees. This ensures sufficient compaction of waste material to achieve dewatering, without clogging the flow path. A lesser angle would significantly detract from the dewatering ability, while a greater angle would significantly increase the tendency to clog. In another embodiment, FIG. 4 shows an adjustable nozzle comprising a pair of doors 92a, 92b, the lower door having a pneumatically biased hinge 93 to render the size of opening 91 pressure responsive. In any case, the restriction applies a compacting force to the disinfected waste before the waste exits the system 10.

Figure 9:
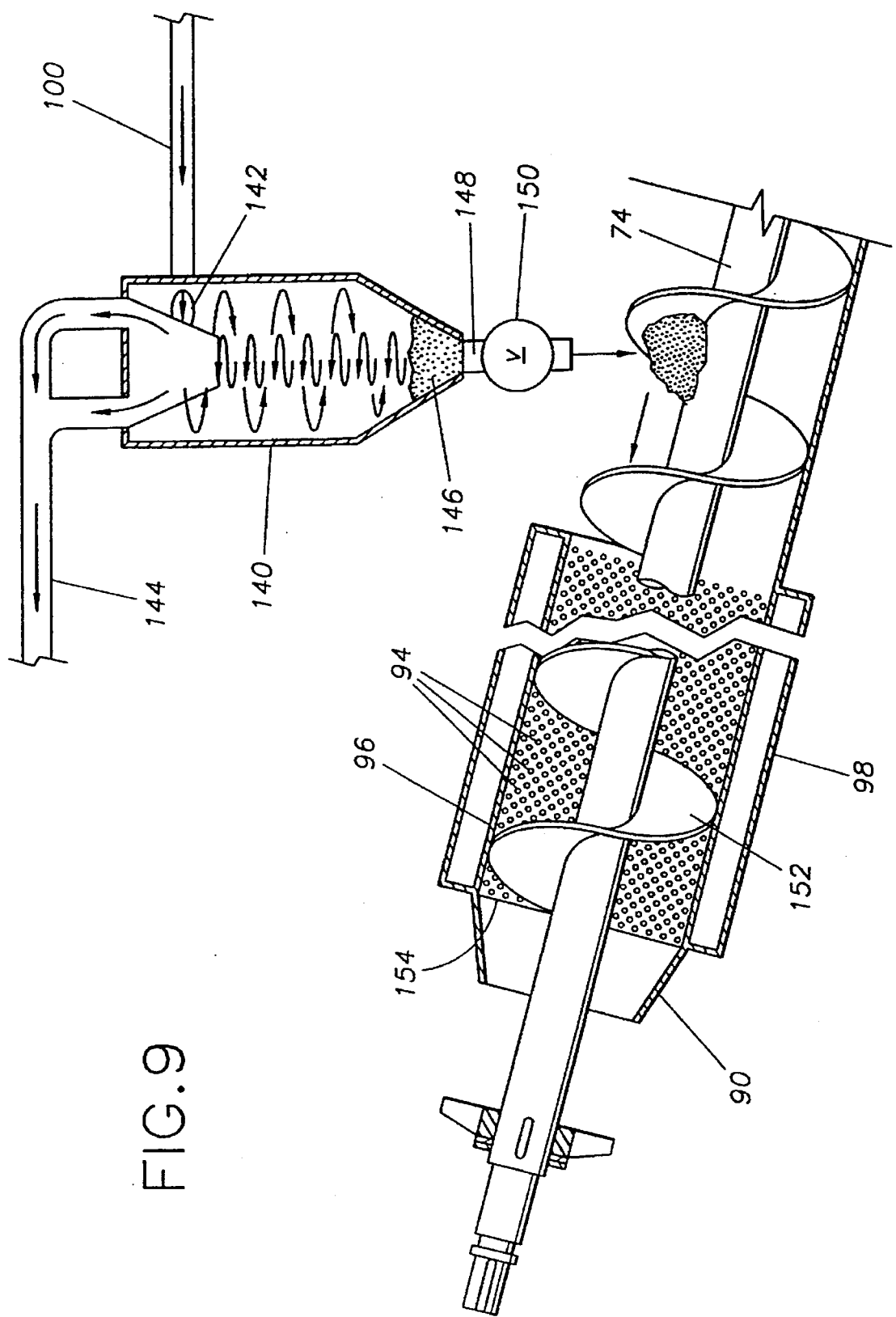
FIG. 9 is a schematic view of the auger of FIG. 1, with a cyclone separator.

Liquid medium driven from the disinfected waste by the compacting force exits auger 74 through perforations 94 in auger housing screen 96. Perforations 94 are sized small enough to restrict the solid waste from the liquid stream. A sleeve 98 around screen 96 at perforations 94 channels the liquid medium into a recycle line 100 which is in fluid communication with the mixing tank 156 through recycle inlet line 144. Before being recycled to the mixing tank 156, as shown in FIG. 9, the liquid is passed through a cyclone separator 140 by means of a pump (not shown). The liquid cycles through the separator 140 to exit into the recycle inlet line 144, after the separation of heavy fines 146 or other materials which fall to the bottom of the separator 140. Periodically, a valve 150 is opened to flush the heavy fines 146 out the outlet 148 of the separator 140 and back onto the waste material on the auger 74.

Collection tank 56 has two chambers 104, 106 in fluid communication with one another, but separated by a weir 108. Port 82 of auger 74 is submerged in primary chamber 104. Secondary chamber 106 receives the overflow of primary chamber 104 and has a recycle outlet port 110 connected to recycle line 54. Heater elements 112, 114 are submerged in primary and secondary chambers 104, 106 respectively for heating the liquid medium as necessary. The collection tank 56 and the mixing tank 156 can be combined as one tank without departing from the spirit of the invention.

Figure 5:
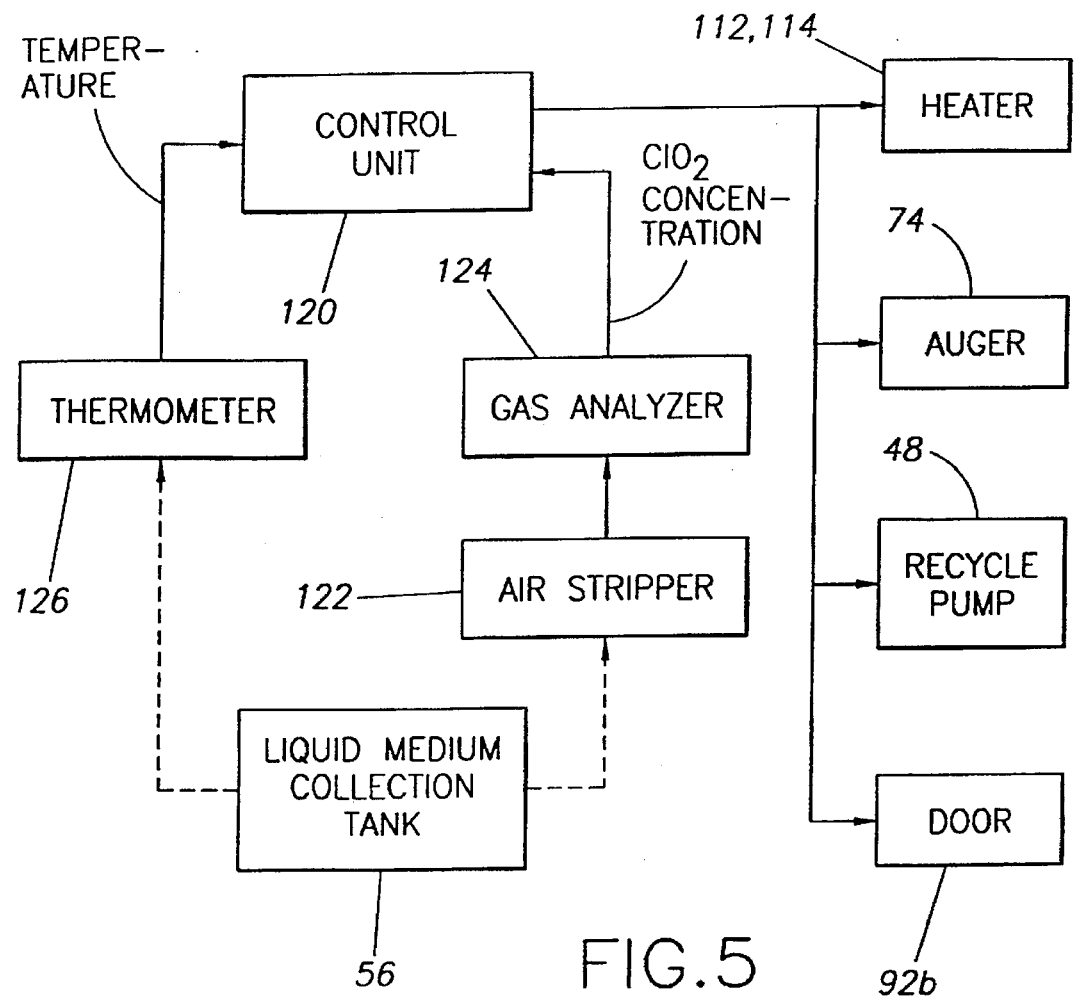
FIG. 5 is a schematic of a control unit for the apparatus of the present invention.

FIG. 5 is a schematic for process control of system 10 which is provided by automated control unit 120 in electrical communication with auger 74, heaters 112, 114, recycle pump 48 and door 92b. If a dewatering cone is used, instead of the adjustable door 92b, this connection to the control unit is deleted. Control unit 120 accordingly regulates the speed of auger screw 80, the heat output of heaters 112, 114, the liquid medium recycle rate of pump 48 and the compaction force applied by door 92b to the waste at solid waste discharge port 86. These parameters are regulated in response to the primary input parameters to unit 120 which are the $ClO_2$ concentration and the temperature of the liquid medium in tank 56. $ClO_2$ concentration data is provided to unit 120 by means of a conventional air stripper 122 in tank 56 and $ClO_2$ gas analyzer 124. Temperature data is provided to unit 120 from a conventional temperature sensor 126.

Method of Operation

With cross-reference to the drawings, operation of system 10 in a continuous mode may be seen. System 10 is particularly suited to the treatment of infectious wastes generated by hospitals and other medical facilities. Such wastes are primarily solid wastes consisting of plastic, paper, fabric, glass, and metal and embody a broad range of medical items including syringes, bottles, tubes, dressings, and the like. "Waste treatment" as the term is used herein constitutes fragmenting of the waste to a relatively small granular particle size and disinfecting the waste to render it substantially innocuous and suitable for ordinary landfilling.

The infectious waste is fed through inlet opening 28 into system 10 in any form. In a preferred embodiment, however, the waste is stored in a sealed compartmentalized plastic bag 128 which is then fed through opening 28 into system 10 in its entirety. Waste bag 128 has a primary compartment 130 containing the infectious waste, and the bag can have other prefilled and sealed compartments 132, 134 containing disinfectant chemicals or other process additives, if required. Additives may include dyes, defoamers, or surfactants.

The waste is inserted through inlet opening 28 into the top of fragmenting chamber 30 by an operator. The waste drops under the force of gravity from opening 28 down into opposingly rotating shredding blades 31a,b, 32a,b, 33a,b of shredding stage 14. The shredding blades destroy waste bag 128, spilling the waste and additives into chamber 30 where they are commingled to form a waste mixture. The shredding blades also break up the frangible waste to a small particle size. Wetting stage 16 operates simultaneously with stage 14, whereby the disinfectant jets wet the waste mixture with a stream of a liquid disinfectant. The liquid disinfectant is pumped to the jets from lines 54 and 62 connected to liquid medium collection tank 56 and mixing tank 156. With efficient operation of dewatering stage 24, the bulk of liquid medium in system 10 is recycled. The liquid disinfectant may be within a temperature range between about 0° C. and 100° C. and preferably between about 5° C. and 70° C. The liquid medium has more preferably been preheated above ambient temperature.

The liquid disinfectant uniformly contacts the falling waste mixture to form a wet mash. The mash falls through metal segregating stage 58 where metals are removed and continues falling down into granulating stage 18 where the rotating blades and the stationary blades break up the already small particle size frangible waste into yet a smaller granular particle size which is preferably slightly less than ¼ inch. The granulating blades also fragment any fibrous material which has not been previously fragmented by the shredding blades, to about the same smaller granular particle size as the frangible material. The granulating blades also more fully mix the mash. Thus, the solids in the resulting mash of granulating stage 18 are preferably fully wetted by the disinfectant solution and the bulk of the solids preferably have a smaller granular particle size which is slightly less than about ¼ inch. The liquid content of the mash is typically on the order of about 60% by weight.

Upon exiting granulating stage 18, the mash drops onto screen 70 which functions in cooperation with the granulating stage 18 to allow the smaller granular particle size waste to fall through it into disinfectant reaction chamber 76 while retaining any waste in granulating stage 18 which has not been sufficiently fragmented. Waste which is retained by screen 70 is scooped up by the rotating granulating blades rotating against screen 70, and returned to cutting surface 68 for additional particle size reduction until it is sufficiently small to pass through screen 70.

Inlet port 78 receives the waste mash from screening stage 20 and directs the mash to reaction chamber 76 integral with auger 74. The disinfectant solution collected in primary chamber 104 contacts the mash at lower end 84 of auger 74. Auger screw 80 turns continuously to withdraw the mash from lower end 84 at angle φ up the auger incline to solid waste discharge port 86 at a controlled rate which allows a sufficient residence time of the mash in reaction chamber 76. A sufficient residence time is typically on the order of less than about 5 minutes and preferably on the order of about 3 minutes. Auger screw 80 also maintains perforated screen 96 free of waste so that the liquid medium may exit the auger to be recycled. The disinfected and dewatered waste exiting system 10 typically has a liquids content of about 20% by weight in contrast to a liquids content in the mash of about 60% by weight.

The bulk waste volume of the exit waste is on the order of about 15% of the inlet waste. Most of the liquid medium is removed from the waste as the result of compaction caused by fixed nozzle 90 or pressure responsive nozzle 92a,b positioned at waste discharge port 86. The liquid medium exits auger 74 through perforations 94 and is collected in tank 156 for recycling to wetting stage 16 via line 162. Alternatively, collection can be in tank 56. The dual-chamber weir arrangement of tank 56 enables collection of fines in primary chamber 104 for periodic removal.

Process control for system 10 is provided by control unit 120. The decontamination level, i.e., level of kill, attainable in system 10 is a function of several interrelated operating parameters including liquid medium flow parameters and auger and heater operating parameters as shown in FIG. 5. Nevertheless, as is shown below, an operational model of system 10 can be developed as a function of a limited number of key parameters, which are level of kill, disinfectant concentration and temperature.

Accordingly, process control can be effected by selecting a desired level of kill, i.e., target kill, and adjusting the disinfectant concentration and disinfectant solution temperature as a function of the operating parameters to meet the preselected target kill. For example, in theory, a target kill of 6 decades ($10^6$ organisms/ml) is achieved within about three minutes for a typical infectious medical waste using a chlorine dioxide solution at a concentration of 30 ppm and a temperature of 50° C. In practice, however, the process is controlled by adjusting only temperature while monitoring variations in the disinfectant concentration as a baseline for temperature adjustment. Temperature is selected as the independent variable and disinfectant concentration as the dependent variable for the practical reason that the ability to independently adjust disinfectant concentration is somewhat limited when a fixed amount of precursor is employed, while it is relatively easy to adjust solution temperature via heaters 112, 114. Added amounts of precursors can be provided for process startup, or in the event of process upsets.

The operational model of system 10 recognizes the functional relationship between solution temperature and concentration of the disinfectant, chlorine dioxide, at a given level of kill n. The model is represented by the equation:

$$[ClO_2] = a_n e^{-k_n T} \quad (1)$$

wherein

[$ClO_2$]=chlorine dioxide concentration,

T=temperature, and $a_n$, $k_n$=empirically determined constants for kill$_n$.

Figure 6:
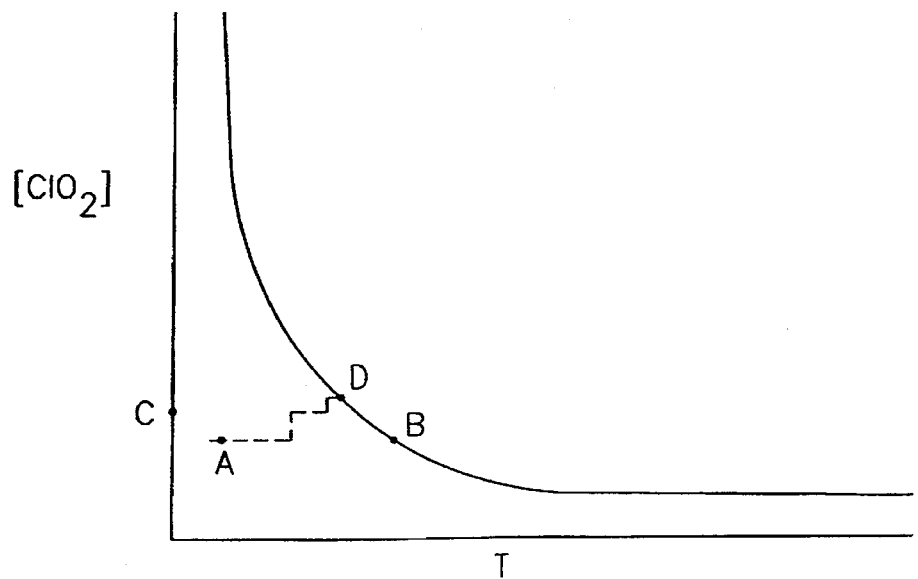
FIG. 6 is a generalized curve for the functional relation between disinfectant solution temperature and disinfectant concentration.

FIG. 6 generally depicts the shape of the curve for equation (1). Each point on the curve defines values of [$ClO_2$] and T at which kill$_n$ can be achieved. Accordingly, process control is more specifically implemented by preselecting the target kill, empirically determining the model constants at the target kill to define a curve, and adjusting the actual values of [$ClO_2$] and T to lie on the target kill curve.

FIG. 6 shows a typical start-up scenario for system 10. The treatment solution is initially at point A which is inside the required curve for the target kill. Since it is desirable to operate on the curve, automated process control 120 consequently raises the temperature of the solution in tanks 56, 156 toward point B which corresponds to the same chlorine dioxide concentration as point A, but at a higher temperature. Raising the temperature of the solution, however, increases the rate of chlorine dioxide formation, thereby increasing the chlorine dioxide concentration of the solution to a value designated by C on the vertical axis. Thus, as point B is approached, control unit 120 calculates that the required temperature on the curve has fallen. The dashed line shows the iterative equilibration procedure followed by control unit 120 whereby an operating point designated by D is ultimately attained. Operation is preferably maintained along or above the locus of points making up the curve which includes point D.

Chlorine dioxide concentration in tank 56 is continuously monitored by means of air stripper 122 and gas analyzer 124 to enable control unit 120 to determine whether the requirements of the disinfectant solution have changed. For example, if a relatively "dirty" waste is fed to system 10, the amount of $ClO_2$ consumed increases, reducing the $ClO_2$ concentration in the solution. Accordingly, control unit 120 must iteratively increase the temperature of the solution in the manner recited above to return operation of system 10 to the curve. If a relatively "clean" waste is fed to system 10, the $ClO_2$ concentration increases, correspondingly reducing the temperature requirement. Thus, control unit 120 decreases the temperature of the solution. It is preferable to preselect a target kill exceeding a minimum acceptable level of kill so that adequate decontamination of the waste is achieved even when operation falls somewhat below the curve. It has generally been found that within the presently prescribed temperature range a minimum $ClO_2$ concentration in the treatment solution to achieve an acceptable level of kill is about 10 ppm up to the required concentration and preferably about 12 ppm up to the required concentration.

Figure 10:
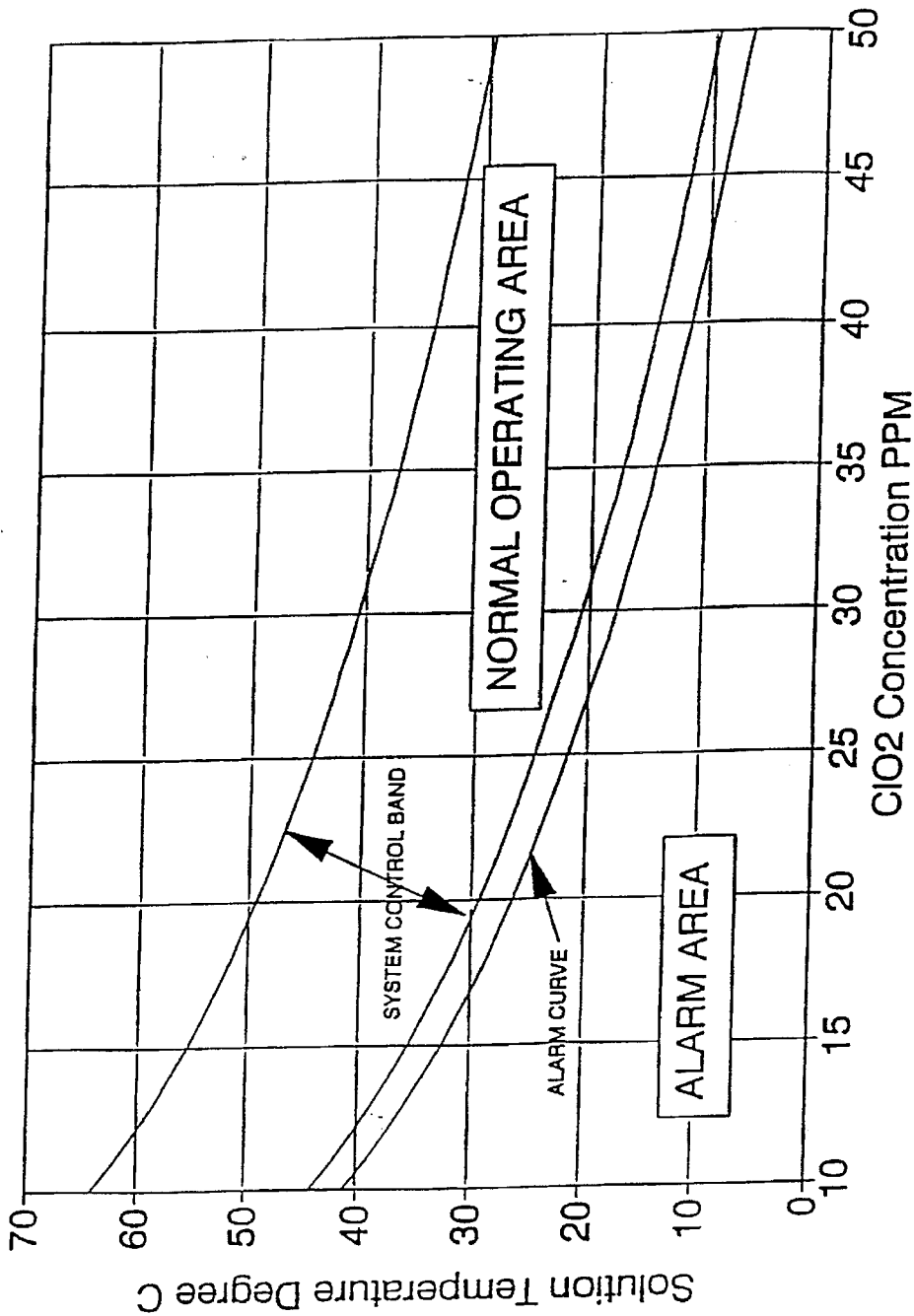
FIG. 10 is a graph showing an operating range of desired disinfectant temperature versus disinfectant concentration.

FIG. 10 shows a typical operating curve which has been found to be effective for practical operation of the apparatus of the present invention. The recommended solution temperature in degrees C is plotted versus the measured chlorine dioxide concentration in ppm. Two curves are shown, reflecting an upper recommended limit and a lower recommended limit, with the area between the curves representing the normal operating area, or system control band. Approximately 3 degrees below the lower recommended limit is an alarm curve. It can be seen from FIG. 10 that the recommended control band for a chlorine dioxide concentration of 30 ppm is between approximately 21 degrees and approximately 41 degrees, with an alarm point at approximately 18 degrees. In fact, the upper recommended temperature limit is 20 degrees above the lower limit for any given concentration. The lower recommended limit curve in FIG. 10 corresponds to the curve shown in FIG. 6.

As noted in the preferred embodiment above, starting quantities of the chlorite salt and acid are fixed. As such, they are preferably provided in stoichiometric excess of quantities necessary to produce the required chlorine dioxide concentrations. Thus, adequate concentrations of liquid precursors will be available in solution for chlorine dioxide production, with equilibrium between the precursors and the reaction products being controlled by tank temperature. A significant fraction of the chlorine dioxide is consumed by reaction with the infectious waste constituents or diffuses out of solution. By way of example, a typical relative starting concentration of precursors, solvent and waste which will provide a desired chlorine dioxide concentration, is on the order of 4.6 g/l sodium chlorite per 3.3 g/l citric acid per 12 kg of solid waste.

While the particular Improved Multi-Stage Infectious Waste Treatment System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. An apparatus for treating infectious waste, comprising:

an inlet opening sized to receive an infectious waste;

a shredding stage positioned to receive the waste from the inlet opening, for shredding the waste to a first, small particle size;

a wetting stage positioned to mix and inject a disinfectant fluid containing a volatile disinfectant into the shredded waste downstream of said shredding stage, said injection occurring substantially at the time of mixing of said volatile disinfectant, to prevent disassociation of said volatile disinfectant;

a granulating stage having rotatable granulator blades positioned to receive the shredded waste from said wetting stage, to granulate the shredded waste to a second, smaller granular particle size and to granulate any strips present in the shredded waste material;

a disinfecting stage positioned to receive the granulated waste from said granulating stage, said disinfecting stage comprising a reaction chamber sized to retain the granulated waste for a selected residence time;

an auger conveyor positioned to transport the granulated waste from said reaction chamber to an exit opening;

a dewatering stage comprising a conical flow restriction in the waste flowpath between said auger conveyor and said exit opening for removing said disinfectant fluid from said waste;

at least one heater for heating said disinfectant fluid; and a control system for sensing the temperature of said disinfectant fluid, for sensing the concentration of said volatile disinfectant in said disinfectant fluid, for selecting an optimum disinfectant temperature corresponding to said disinfectant concentration, and for controlling said at least one heater to maintain said temperature of said disinfectant in a control band above said selected optimum temperature, to achieve a desired organism kill rate.

2. An apparatus for treating infectious waste as recited in claim 1, further comprising:

a collection tank for collecting said disinfectant fluid;

an air stripper for stripping gases from said disinfectant fluid in said collection tank; and a gas analyzer for analyzing said gases stripped from said collection tank to determine said concentration of said volatile disinfectant.

3. An apparatus for treating infectious waste as recited in claim 2, wherein said at least one heater is located in said collection tank.

4. An apparatus for treating infectious waste as recited in claim 1, wherein said control band has a band width of approximately 20 degrees Celsius.

5. An apparatus for treating infectious waste, comprising:

an inlet opening sized to receive an infectious waste;

a shredding stage positioned to receive the waste from the inlet opening, for shredding the waste to a first, small particle size;

a wetting stage positioned to mix and inject a disinfectant fluid containing a volatile disinfectant into the shredded waste downstream of said shredding stage, said injection occurring substantially at the time of mixing of said volatile disinfectant, to prevent disassociation of said volatile disinfectant;

a granulating stage having rotatable granulator blades positioned to receive the shredded waste from said wetting stage, to granulate the shredded waste to a second, smaller granular particle size and to granulate any strips present in the shredded waste material;

a disinfecting stage positioned to receive the granulated waste from said granulating stage, said disinfecting stage comprising a reaction chamber sized to retain the granulated waste for a selected residence time;

an auger conveyor positioned to transport the granulated waste from said reaction chamber to an exit opening;

a dewatering stage comprising a conical flow restriction in the waste flowpath between said auger conveyor and said exit opening, for removing said disinfectant fluid from said waste;

a collection tank for collecting said disinfectant fluid;

a temperature sensor in said collection tank for sensing the temperature of said disinfectant fluid;

at least one heater located in said collection tank for heating said disinfectant fluid;

an air stripper for stripping gases from said disinfectant fluid in said collection tank;

a gas analyzer for analyzing said gases stripped from said collection tank to determine a concentration of said volatile disinfectant in said disinfectant fluid; and a control unit for receiving the temperature of said disinfectant fluid from said temperature sensor, for receiving the concentration of said volatile disinfectant from said gas analyzer, for selecting an optimum disinfectant temperature corresponding to said disinfectant concentration, and for controlling said at least one heater to maintain said temperature of said disinfectant fluid in a control band above said selected optimum temperature, to achieve a desired organism kill rate.

6. An apparatus for treating infectious waste as recited in claim 5, wherein said control band has a band width of approximately 20 degrees Celsius.

* * * * *